(12) United States Patent
Bokel et al.

(10) Patent No.: US 6,812,353 B2
(45) Date of Patent: Nov. 2, 2004

(54) CHROMANONE DERIVATIVES

(75) Inventors: Heinz-Hermann Bokel, Darmstadt (DE); Christoph Muermann, Reinheim (DE); Uschi Schmid-Grossmann, Bensheim (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

(21) Appl. No.: 10/363,774

(22) PCT Filed: Aug. 28, 2001

(86) PCT No.: PCT/EP01/09900

§ 371 (c)(1),
(2), (4) Date: Jul. 29, 2003

(87) PCT Pub. No.: WO02/20507

PCT Pub. Date: Mar. 14, 2002

(65) Prior Publication Data

US 2004/0092579 A1 May 13, 2004

(30) Foreign Application Priority Data

Sep. 7, 2000 (DE) .......................... 100 44 091

(51) Int. Cl.[7] ............................. C07D 311/04
(52) U.S. Cl. ...................... 549/399; 514/456
(58) Field of Search ............ 549/399; 514/456

(56) References Cited

U.S. PATENT DOCUMENTS

| | | | |
|---|---|---|---|
| 4,479,007 A | 10/1984 | Kabbe | |
| 5,767,132 A | 6/1998 | Böttcher et al. | |
| 6,646,136 B1 | 11/2003 | Bokel et al. | |

FOREIGN PATENT DOCUMENTS

| | | |
|---|---|---|
| DE | 2611910 | 9/1977 |
| DE | 19858341 | 6/2000 |
| EP | 707007 A1 * | 4/1996 |
| EP | 0707007 | 4/1996 |
| WO | WO 02/20507 A1 * | 3/2002 |

OTHER PUBLICATIONS

Document N supplied by applicant. Document O cited in the specification. Therefore copies not provided.*
J. F. W. Mcomie, "Protective groups in organic chemistry," 1973, pp. 46–61, Plenum Publishing Company Ltd., London.

* cited by examiner

*Primary Examiner*—Amelia Owens
(74) *Attorney, Agent, or Firm*—Millen, White, Zelano & Branigan, P.C.

(57) ABSTRACT

Chromanone derivatives of the formula I

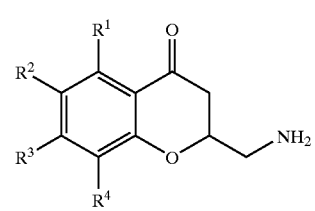

in which
$R^1$ to $R^4$ are each, independently of one another, H, A, CN, Hal, $OR^5$, $COOR^5$, $CF_3$, $OCF_3$, $NO_2$, Ar, OAr, $N(R^5)_2$ or $CON(R^5)_2$,
$R^5$ is H or A,
A is alkyl having 1 to 6 carbon atoms,
Ar is phenyl which is unsubstituted or substituted by A, $OR^5$, CN, Hal, $CF_3$, $OCF_3$, $NO_2$ or $N(R^5)_2$,
Hal is F, Cl, Br or I,
and their salts, are suitable as intermediates in the synthesis of medicaments.

12 Claims, No Drawings

CHROMANONE DERIVATIVES

The invention relates to chromanone derivatives of the formula I

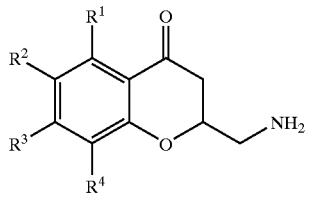

in which
R¹ to R⁴ are each, independently of one another, H, A, CN, Hal, OR⁵, COOR⁵, CF₃, OCF₃, NO₂, Ar, OAr, N(R⁵)₂ or CON(R⁵)₂,
R⁵ is H or A,
A is alkyl having 1 to 6 carbon atoms,
Ar is phenyl which is unsubstituted or substituted by A, OR⁵, CN, Hal, CF₃, OCF₃, NO₂ or N(R⁵)₂,
Hal is F, Cl, Br or I,
and their salts.

The invention also relates to the optically active forms, the racemates, the enantiomers, and the hydrates and solvates, for example alcoholates, of these compounds.

Similar compounds are disclosed in EP 0 707 007.

The invention had the object of finding novel compounds which can be used, in particular, as Intermediates in the synthesis of medicaments.

It has been found that the compounds of the formula I and their salts are important intermediates for the preparation of medicaments, in particular those which exhibit actions on the central nervous system.

The invention relates to the chromanone derivatives of the formula I and their salts.

Above and below, the radicals R¹, R², R³, R⁴, R⁵ and R⁶ have the meanings indicated under the formulae I to III, unless expressly stated otherwise.

In the above formulae, A is alkyl, is linear or branched, and has 1 to 6, preferably 1, 2, 3, 4, 5 or 6 carbon atoms. A is preferably methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. A is particularly preferably methyl.

Acyl has 1 to 6 carbon atoms, preferably 1, 2, 3 or 4 carbon atoms. Acyl is in particular acetyl, propionyl or butyryl.

Ar is phenyl which is unsubstituted or monosubstituted, disubstituted or trisubstituted by A, CF₃, OR⁵, OCF₃, CN, NO₂, Hal or N(R⁵)₂, where R⁵ is H or A, and A is as defined above. Ar is preferably phenyl.

Hal is preferably F, Cl or Br.

R¹, R², R³ and R⁴ are each, independently of one another, H, A, CN, Hal, OR⁵, COOR⁵, CF₃, OCF₃, NO₂, Ar, OAr, N(R⁵)₂ or CON(R⁵)₂, where A, Hal, Ar and R⁵ are as defined above. R¹ is preferably H. R² is particularly preferably H. R³ is preferably H. R⁴ is preferably H.

R⁶ is acyl having 1 to 6 carbon atoms, —CO—Ar or an amino-protecting group, where acyl and Ar are as defined above. R⁶ is particularly preferably acyl.

The term "amino-protecting group" is known in general terms and relates to groups which are suitable for protecting (blocking) an amino group against chemical reactions. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1–20 carbon atoms, in particular 1–8 carbon atoms. The term "acyl group" should be understood in the broadest sense in connection with the present process. It covers acyl groups derived from aliphatic, araliphatic, alicyclic, aromatic or heterocyclic carboxylic acids or sulfonic acids and, in particular, alkoxycarbonyl, alkenyloxycarbonyl, aryloxycarbonyl and especially aralkoxycarbonyl groups. Examples of acyl groups of this type are alkanoyl, such as acetyl, propionyl and butyryl; aralkanoyl, such as phenylacetyl; aroyl, such as benzoyl or toluyl; aryloxy-alkanoyl, such as phenoxyacetyl; alkoxycarbonyl, such as methoxycarbonyl, ethoxycarbonyl, 2,2,2-trichloroethoxycarbonyl, BOC or 2-iodoethoxycarbonyl; alkenyloxycarbonyl, such as allyloxycarbonyl (Aloc), aralkoxycarbonyl, such as CBZ (synonymous with Z), 4-methoxybenzyloxycarbonyl (MOZ), 4-nitrobenzyloxycarbonyl or 9-fluorenylmethoxycarbonyl (Fmoc); 2-(phenylsulfonyl)ethoxycarbonyl; trimethylsilylethoxycarbonyl (Teoc), or arylsulfonyl, such as 4-methoxy-2,3,6-trimethylphenylsulfonyl (Mtr). Preferred amino-protecting groups are BOC, Fmoc and Aloc, furthermore CBZ, benzyl and acetyl. Particularly preferred protecting groups are BOC and Fmoc.

The compounds of the formula I can have one or more chiral centres and therefore occur in various stereoisomeric forms. The formula I covers all these forms.

Particularly preferred compounds of the formula I are a) 2-aminomethyl-4-chromanone, b) (R)-2-aminomethyl-4-chromanone, c) (S)-2-aminomethyl-4-chromanone, and their salts.

The invention furthermore relates to a process for the preparation of chromanone derivatives of the formula I according to claim 1 and of their salts, characterised in that a compound of the formula II

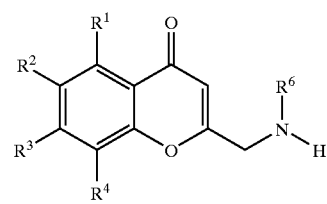

in which

R¹, R², R³ and R⁴ are as defined in claim 1, and

R⁶ is acyl having 1 to 6 carbon atoms, —CO—Ar or an amino-protecting group, is hydrogenated with the aid of a non-racemic chiral catalyst to give a compound of the formula III

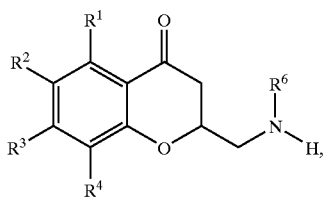

in which R¹ to R⁶ are as defined above, and the radical R⁶ is cleaved off.

In particular, it has been found that (2-acetylaminomethyl)chromen-4-one can be hydrogenated with various non-racemic chiral rhodium/diphosphine complexes to give enantiomerically enriched (2-acetylaminomethyl)chroman-4-one, and the acetyl group can be cleaved off while avoiding racemisation.

The invention also relates to a process for the preparation of chromanone derivatives of the formula I, characterised in that the non-racemic chiral catalyst is a transition-metal complex.

The catalyst is particularly preferably a transition-metal complex containing a metal selected from the group consisting of rhodium, iridium, ruthenium and palladium.

The invention furthermore relates to a process for the preparation of chromanone derivatives of the formula I, characterised in that the catalyst is a transition-metal complex in which the transition metal is complexed with a chiral diphosphine ligand.

The following ligands may be mentioned by way of example:

(S)-EtDuphos:

(S)-BINAP:

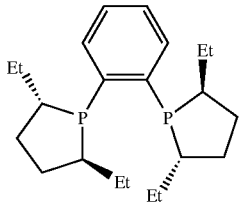

(S)-TolBINAP:

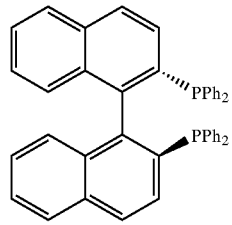

where Tol is 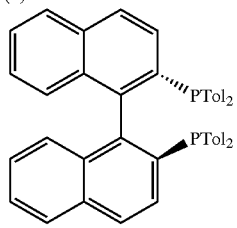

(S,S)-Chiraphos:

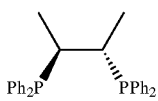

(S,S)-DIOP:

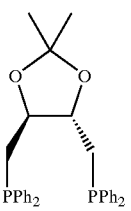

(S,S)-Skewphos (BDPP):

(S,S)-BPPM:

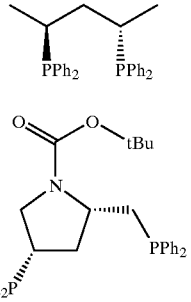

(R,R)-Norphos:

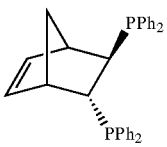

(S,R)-BPPFOH:

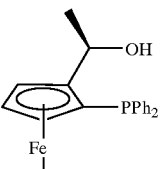

(S,R)-PFctBu:

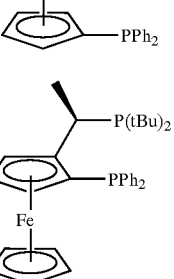

Depending on the choice of the R) or (S)-enantiomer of the ligand in the catalyst, the (R)- or (S)-enantiomer is obtained in excess.

Precursors for the chiral ligands are compounds such as, for example, Rh(COD)₂OTf (cyclooctadienylrhodium triflate), [Rh(COD)Cl]₂, Rh(COD)₂BF₄, [Ir(COD)Cl]₂, Ir(COD)₂BF₄ or [Ru(COD)Cl₂]ₓ.

The compounds of the formula I and also the starting materials for their preparation are furthermore prepared by chemical reactions which are known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ, so that they are not isolated from the reaction mixture, but are instead immediately converted further into the compounds of the formula I.

Some of the compounds of the formula II are known; the unknown compounds can easily be prepared analogously to the known compounds. The conversion of a compound of the formula II into a compound of the formula I is carried out in accordance with the invention using hydrogen gas with the aid of a non-racemic chiral catalyst in an inert solvent, such as, for example, methanol or ethanol, followed by racemisation-free removal of the radical $R^6$, as defined above.

Suitable inert solvents are furthermore, for example, hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as isopropanol, n-propanol, n-butanol or tert-butanol; ethers, such as diethyl ether, diisopropyl ether, tetrahydrofuran (THF) or dioxane; glycol ethers, such as ethylene glycol monomethyl monoethyl ether, ethylene glycol dimethyl ether (diglyme); ketones, such as acetone or butanone; amides, such as acetamide, dimethylacetamide or dimethylformamide (DMF); nitrites, such as acetonitrile; esters, such as ethyl acetate, if desired also mixtures of the said solvents with one another or mixtures with water.

The reaction time in the enantioselective hydrogenation is between a few minutes and 14 days, depending on the conditions used, and the reaction temperature is between 0 and 150°, normally between 20 and 130°.

The catalyst/substrate ratio is usually between 1:100000 and 1:10, particularly preferably from 1:10000 to 1:100. The reaction time is then, for example, between 3 and 20 hours. The hydrogenation is carried out under 1–200 bar of hydrogen, preferably at 3–100 bar.

The racemisation-free removal of the radical $R^6$, where $R^6$ is acyl, is carried out, for example, using NaOH or KOH in water, water/THF, water/dioxane or aqueous hydrochloric acid at temperatures between 0 and 100°.

The liberation of the compounds of the formula I from their functional derivatives, i.e. the removal of the radical $R^6$, where $R^6$ is an amino-protecting group, is known from the literature for the respective protecting group used (for example T. W. Greene, P. G. M. Wuts, *Protective Groups in Organic Chemistry*, 2nd Edn., Wiley, New York, 1991 or P. J. Kocienski, *Protecting Groups*, 1st Edn., Georg Thieme Verlag, Stuttgart-New-York, 1994). Use can also be made here of variants which are known per se, but are not mentioned here in greater detail.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

The invention furthermore relates to the use of the compounds of the formula I as intermediates for the synthesis of medicaments. Corresponding medicaments, which preferably have actions on the central nervous system, are described, for example, in EP 0 707 007.

The invention accordingly relates in particular to the use of the compounds of the formula I according to claim 1 in the synthesis of (R)-2-[5-(4-fluorophenyl)-3-pyridylmethylaminomethyl]chromane and its salts, characterised in that a) a compound of the formula II

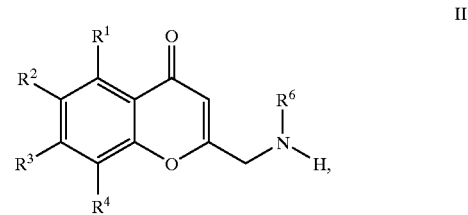

in which $R^1$, $R^2$, $R^3$ and $R^4$ are H, and $R^6$ is as defined in claim 4, is hydrogenated with the aid of a non-racemic chiral catalyst to give a compound of the formula III

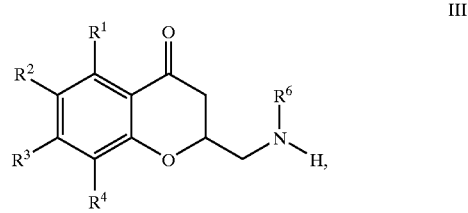

in which $R^1$ to $R^6$ are as defined above, in that b) the enantiomerically pure (R)-compound of the formula IIIa

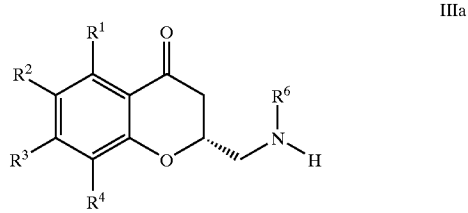

is obtained by crystallisation from the resultant enantiomerically enriched mixture of the (R)- and (S)-compounds of the formula III, in which $R^1$ to $R^6$ are as defined above, in that c) the radical $R^6$ is removed from the resultant (R)-compound of the formula IIIa, in which $R^1$ to $R^6$ are as defined above, to give an enantiomerically pure (R)-compound of the formula I

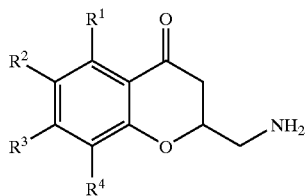

in which R¹, R², R³ and R⁴ are H, or a salt of this compound, in that d) the enantiomerically pure (R)-compound of the formula I in which R¹ to R⁴ are H is reduced in the usual way to give (R)-aminomethylchromane, in that e) the resultant (R)-(chroman-2-ylmethyl)amine is converted into its acid-addition salt, and the latter is converted in a known manner into (R)-2-[5-(4-fluorophenyl)-3-pyridylmethylaminomethyl]chromane and optionally into its acid-addition salt, it also being possible to carry out the isolation of the (R)-enantiomer from the enantiomerically enriched (R,S)-mixture by crystallisation after step c) or after step d).

The invention furthermore relates to the use of the compounds of the formula I as intermediates for the synthesis of medicaments which exhibit actions on the central nervous system.

The carbonyl group in the compounds of the formula I according to the invention can be reduced for the preparation of the corresponding chromane derivatives of the formula I by a Wolff-Kishner reduction (for example Paradkar, M. V. et al, in J. Chem. Res., Synop. 1998, 6, 318–319) under conventional reaction conditions or by noble metal-catalysed hydrogenation (for example P. N. Rylander, Hydrogenation Methods, Best Synthetic Methods, Academic Press, 1985) under conventional reaction conditions.

The (R)-(chroman-2-ylmethyl)amine synthesised from the compound of the formula I according to the invention in which R¹ to R⁴ are H by Wolff-Kishner reduction or noble metal-catalysed hydrogenation is converted into its acid-addition salt by a method indicated above, and this can be converted into (R)-2-[5-(4-fluorophenyl)-3-pyridylmethylaminomethyl]chromane in a known manner (lit.: EP 0 707 007).

(Chroman-2-ylmethyl)amine can likewise be prepared from a compound of the formula III in which R¹ to R⁴ are H in accordance with the following reaction sequence 1:

Reaction sequence 1:

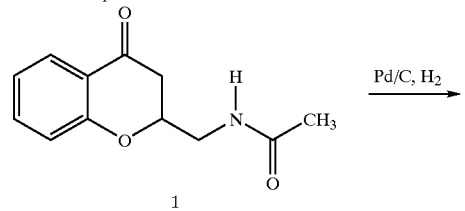

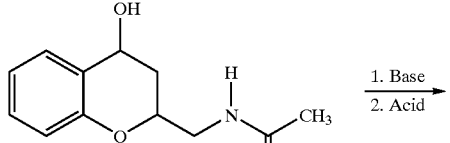

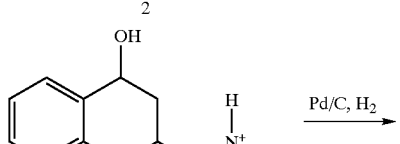

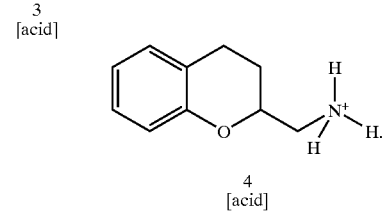

Starting from the compound N-(4-oxochroman-2-ylmethyl)acetamide 1, the carbonyl group is hydrogenated to the hydroxyl group with noble-metal catalysis, for example using Pd on carbon (50% water-moist), to give the compound N-(4-hydroxychroman-2-ylmethyl)acetamide 2. The acetyl group is cleaved off using a base, for example sodium hydroxide. Addition of an acid gives the acid-addition salt 3 of 2-aminomethylchroman-4-ol. A further noble metal-catalysed hydrogenation generates the acid-addition salt 4 of 2-aminomethylchromane.

Reaction of the enantiomerically pure compounds, i.e. reaction of (R)-N-(4-oxochroman-2-ylmethyl)acetamide, with hydrogen with noble-metal catalysis gives (R)-N-(4-hydroxychroman-2-ylmethyl)acetamide. Subsequent removal of the acetyl group gives (R)-2-aminomethylchroman-4-ol and, depending on the work-up, its salts. Noble metal-catalysed reduction gives (R)-2-aminomethylchromane, and, depending on the work-up, its salts. Analogous intermediates in the reaction of (S)-N-(4-oxochroman-2-ylmethyl)acetamide are (S)-N-(4-hydroxychroman-2-ylmethyl)acetamide and (S)-2-aminomethylchroman-4-ol.

The invention therefore likewise relates to the compounds
a) N-(4-hydroxychroman-2-ylmethyl)acetamide,
b) 2-aminomethylchroman-4-ol,
c) (R)-N-(4-hydroxychroman-2-ylmethyl)acetamide,
d) (R)-2-aminomethylchroman-4-ol,
e) (S)-N-(4-hydroxychroman-2-ylmethyl)acetamide and
f) (S)-2-aminomethylchroman-4-ol.

The invention furthermore relates to the use of the above-described compounds a) to f) in the synthesis of (R)-2-[5-(4-fluorophenyl)-3-pyridylmethylaminomethyl]chromane and its salts.

It is furthermore possible to prepare (R/S)-2-aminomethylchromane and its salts, in enantiomerically pure form or as a racemate, directly in a one-pot reaction from N-(4-oxochroman-2-ylmethyl)acetamide by amide cleavage followed by reduction.

Above and below, all temperatures are given in ° C. In the following examples, "conventional work-up" means that water is added if necessary, the pH is, if necessary, adjusted to a value of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel.

EXAMPLE 1

(1) 35.1 g of N-(4-oxochroman-2-ylmethyl)acetamide are suspended in 90 ml of toluene, and 1.6 ml of a 10 millimolar solution consisting of [Rh((S)-ToIBINAP)(COD)Cl] in toluene, are added under inert conditions. This suspension is hydrogenated in an autoclave at 100 bar of hydrogen and 100° C. After 12 hours, enantiomerically pure (>99% ee) (R)-N-(4-oxochroman-2-ylmethyl)acetamide is crystallised by cooling to room temperature. Drying gives 31.04 g of (R)-N-(4-oxochroman-2-ylmethyl)acetamide.

(2) 3.7 g of sodium hydroxide are dissolved in 80 ml of water. After addition of 10.13 g of (R)-N-(4-oxochroman-2-ylmethyl)acetamide, the mixture is refluxed for 20 hours. After cooling, the aqueous phase is extracted three times with MTB ether (methyl tert-butyl ether), and the solvent is subsequently distilled off under reduced pressure. The residue is taken up in 50 ml of ethanol, and 4.7 ml of 37% HCl are added. The precipitated (R)-2-aminomethylchroman-4-one hydrochloride is filtered off and dried. Yield 9.55 g.

EXAMPLE 2

Preparation of R)-2-aminomethylchromane from (R)-2-aminomethylchroman-4-one hydrochloride for the further synthesis of (R)-2-[5-(4-fluorophenyl)-3-pyridylmethylaminomethyl]chromane and its salts analogously to EP 0 707 007:

9.55 g of (R)-2-aminomethylchroman-4-one hydrochloride are hydrogenated at 50° C. and 7 bar of hydrogen with 950 mg of 5% Pd/carbon (50% water-moist) in 100 ml of methanol to give (R)-2-aminomethylchromane. The hot-filtered solution is evaporated to 50 ml and cooled, and the precipitated product (R)-2-aminomethylchromane is filtered off and dried (yield: 8.04 g).

EXAMPLE 3

Alternative synthesis for the preparation of (R)-2-aminomethylchromane from N-(4-oxochroman-2-ylmethyl)acetamide for the further synthesis of (R)-2-[5-(4-fluorophenyl)-3-pyridylmethylaminomethyl]chromane and its salts analogously to EP 0 707 007:

(1) 20.9 g of N-(4-oxochroman-2-ylmethyl)acetamide are dissolved in 70 ml of toluene at 70° C. and hydrogenated for 15 hours at 70° C. and 3 bar of hydrogen with 2 g of 5% Pd/carbon (50% water-moist). The warm hydrogenation solution is filtered, and the compound (R)-N-(4-hydroxychroman-2-ylmethyl)acetamide crystallises at −10° C. Drying gives 19. g of (R)-N-(4-hydroxychroman-2-ylmethyl)acetamide.

(2) 18.99 g of (R)-N-(4-hydroxychroman-2-ylmethyl)acetamide and 7.5 g of sodium hydroxide are heated at the reflux temperature for 15 hours in 150 ml of water. The product is subsequently extracted with MTB ether, the solution is evaporated, and the residue is taken up in 80 ml of ethanol. After addition of 10 ml of 37% HCl, the hydrochloride of (R)-2-aminomethylchroman-4-ol precipitates. Drying gives a yield of 19.26 g.

(3) 19.2 g of (R)-2-aminomethylchroman-4-ol hydrochloride are dissolved in 300 ml of methanol and hydrogenated at 50° C. and 7 bar with 2 g of 5% Pd/carbon (50% water-moist). After filtration and evaporation of the filtrate, (R)-2-aminomethylchromane crystallises (yield 15.5 g).

EXAMPLE 4

One-pot synthesis for the preparation of R)-2-aminomethylchromane from N-(4-oxochroman-2-ylmethyl)acetamide for the further synthesis of (R)-2-[5-(4-fluorophenyl)-3-pyridylmethylaminomethyl]chromane and its salts analogously to EP 0 707 007:

100 ml of 5.8 M HCl are added to 7.85 g of N-(4-oxochroman-2-ylmethyl)acetamide and 1.0 g of 5% Pd/carbon (50% water-moist), and the mixture is heated at 110° C. for 24 hours in an autoclave. The mixture is then cooled to 50° C., and 3 bar of hydrogen are injected. The hydrogenation is complete after 16 hours, and, after filtration and crystallisation, 4.1 g of (R)-2-aminomethylchromane are isolated.

What is claimed is:

1. A compound of formula I

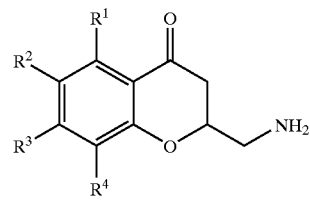

wherein $R^1$ to $R^4$ are each, independently of one another, H, A, CN, Hal, $OR^5$, $COOR^5$, $CF_3$, $OCF_3$, $NO_2$, Ar, OAr, $N(R^5)_2$ or $CON(R^5)_2$, $R^5$ is H or A, A is alkyl having 1 to 6 carbon atoms, Ar is phenyl which is unsubstituted or substituted by A, $OR^5$, CN, Hal, $CF_3$, $OCF_3$, $NO_2$, or $N(R^5)_2$, Hal is F, Cl, Br or I, or a salt thereof.

2. An enantiomer of the compound of the formula I.

3. A compound of the formula I according to claim 1:

a) 2-aminomethyl-4chromanone, b) (R)-2-aminomethyl-4-chromanone, c) (S)-2-aminomethyl-4-chromanone, or a salt thereof.

4. A process for the preparation of a compound of the formula I according to claim 1 or a salt thereof, wherein a compound of the formula II

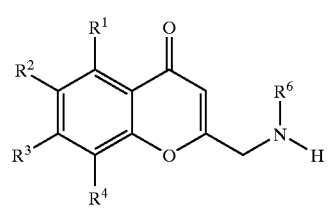

wherein $R^1$, $R^2$, $R^3$ and $R^4$ are as defined in claim 1, and $R^6$ is an acyl having 1 to 6 carbon atoms, —CO—Ar or an amino-protecting group, is hydrogenated with the aid of a non-racemic chiral catalyst to give a compound of the formula III

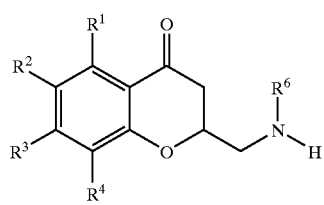

wherein the radical R⁶ is cleaved off.

5. A process for the preparation of a compound of the formula I according to claim 4, wherein the catalyst is a transition-metal complex.

6. A process for the preparation of a compound of the formula I according to claim 4, wherein the catalyst is a transition-metal complex containing rhodium, iridium, ruthenium or palladium.

7. A process for the preparation of a compound of the formula I according to claim 4, wherein the catalyst is a transition-metal complex in which the transition metal is complexed with a chiral diphosphine ligand.

8. A method for synthesizing (R)-2-[5-(4-fluorophenyl)-3-pyridylmethylaminomethyl]chromane or a salt thereof, comprising hydrogenating with the acid of a non-racemic chiral catalyst a) a compound of the formula

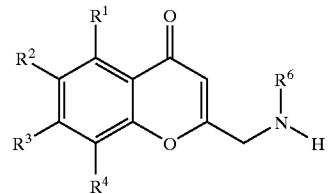

in which R¹, R², and R⁴ are H, and R⁶ is an acyl having 1–6 carbon atoms, —CO—Ar or an amino-protecting group, to give a compound of the formula III

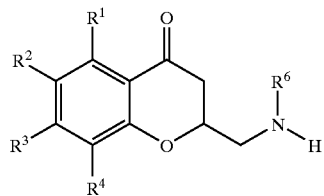

b) crystallizing the resultant enantiomerically enriched mixture of the (R)- and (S)-compounds of the formula III, to obtain the enantiomerically pure (R)-compound of the formula IIIa

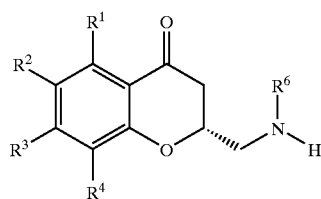

c) removing the radical R⁶ from the resultant (R)-compound of the formula IIIa, to give an enantiomerically pure compound of the formula I

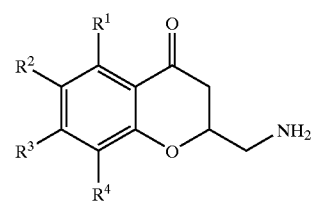

or a salt of this compound, d) reducing the enantiomerically pure (R)-compound of the formula I wherein R¹ to R⁴ are H to give (R)-aminomethylchromane, e) converting the resultant (R)-(chroman-2-ylmethyl) amine into its acid-addition salt, and converting the latter into (R)-2-[5-(4-fluorophenyl)-3-pyridylmethylaminomethyl]chromane and optionally into its acid-addition salt, or carrying out the isolation of the (R)-enantiomer from the enantiomerically enriched (R,S)-mixture by crystallisation after step c) or after step d).

9. A compound according to claim 1, wherein A is methyl, Ar is phenyl, and Hal is F, Cl, or Br.

10. A compound according to claim 1, wherein R¹–R⁴ are H.

11. A process according to claim 4, wherein R⁶ is acyl.

12. A process according to claim 4, wherein R⁶ is butoxycarbonyl or 9-fluorenylmethoxy carbonyl.

* * * * *